(12) United States Patent
Zeller

(10) Patent No.: US 12,235,339 B2
(45) Date of Patent: Feb. 25, 2025

(54) FAT SUPPRESSION USING NEURAL NETWORKS

(71) Applicant: Siemens Healthcare GmbH, Erlangen (DE)

(72) Inventor: Mario Zeller, Erlangen (DE)

(73) Assignee: Siemens Healthineers AG, Erlangen (DE)

( * ) Notice: Subject to any disclaimer, the term of this patent is extended or adjusted under 35 U.S.C. 154(b) by 402 days.

(21) Appl. No.: 17/879,062

(22) Filed: Aug. 2, 2022

(65) Prior Publication Data

US 2023/0041796 A1    Feb. 9, 2023

(30) Foreign Application Priority Data

Aug. 3, 2021   (DE) .................. 102021208406.0

(51) Int. Cl.

| | |
|---|---|
| *G01R 33/56* | (2006.01) |
| *A61B 5/00* | (2006.01) |
| *A61B 5/055* | (2006.01) |
| *G01R 33/48* | (2006.01) |
| *G06N 3/02* | (2006.01) |

(52) U.S. Cl.
CPC .......... *G01R 33/5608* (2013.01); *A61B 5/055* (2013.01); *A61B 5/7267* (2013.01); *G01R 33/4828* (2013.01); *G06N 3/02* (2013.01)

(58) Field of Classification Search
CPC ............ G01R 33/5608; G01R 33/4828; A61B 5/055; A61B 5/7267; G06R 3/02
USPC ....................................................... 382/128
See application file for complete search history.

(56) References Cited

U.S. PATENT DOCUMENTS

| | | | | |
|---|---|---|---|---|
| 8,928,319 | B2* | 1/2015 | Feiweier | G01R 33/56341 |
| | | | | 324/309 |
| 10,598,746 | B2* | 3/2020 | Bauer | G01R 33/4828 |
| 2005/0215882 | A1* | 9/2005 | Chenevert | G01R 33/4828 |
| | | | | 600/410 |
| 2015/0309137 | A1* | 10/2015 | Bydder | G01R 33/34 |
| | | | | 324/309 |

(Continued)

OTHER PUBLICATIONS

Kato et al.:"Declaration of Financial Interests or Relationships", One Community, ISMR&SMRT, Virtual Conference&Exhibition, Aug. 8-14, 2020.

(Continued)

*Primary Examiner* — William D Titcomb
(74) *Attorney, Agent, or Firm* — Banner & Witcoff Ltd.

(57) ABSTRACT

In a method for determining a fat-reduced MR image, a first MR image is provided having, apart from the other tissue constituents, MR signals from only one of the two fat constituents, the first MR image is applied to a trained ANN, which was trained by first MR training data as the input data, the training data including, apart from the other tissue constituents, MR signals from only the one of the two fat constituents, and using second MR training data as a base knowledge, the second MR training data including, apart from the other tissue constituents, no MR signals from the two fat constituents; and an MR output image is determined from the trained ANN, to which the first MR image was applied, as a fat-reduced MR image, wherein the fat-reduced MR image includes, apart from the other tissue constituents, no MR signals from the two fat constituents.

20 Claims, 3 Drawing Sheets

(56) References Cited

U.S. PATENT DOCUMENTS

| | | | | |
|---|---|---|---|---|
| 2016/0066874 | A1* | 3/2016 | Huang | A61B 6/037 |
| | | | | 600/411 |
| 2017/0371010 | A1* | 12/2017 | Shanbhag | G01R 33/243 |
| 2020/0271741 | A1* | 8/2020 | Paul | G01R 33/4835 |
| 2020/0386838 | A1* | 12/2020 | Miyazaki | G01R 33/5607 |
| 2021/0364587 | A1* | 11/2021 | De Weerdt | G01R 33/5611 |
| 2023/0384407 | A1* | 11/2023 | Tong | G06T 7/0012 |

OTHER PUBLICATIONS

Wikipedia "U-Net" https://en.wikipedia.org/wiki/U-Net (downloaded Nov. 13, 2020).
Basty, Nikolas: "Swap-Free Fat-Water Separation in Dixon MRI using Conditional Generative Adversarial Networks"; In: Electrical Engineering and Systems Scienec > Image and Video Processing; pp. 1-12; https://arxiv.org/abs/2107.14175.
Yu, Huanzhou et al:"Combination of Complex-Based and Magnitude-Based Multiecho Water-Fat Separation for Accurate Quantification of Fat-Fraction"; Magn Reson Med., vol. 66, No. 1, pp. 199-206; Jul. 2011.
Burakiewicz, Jedrzej et al: "Water-Fat Separation in Diffusion-Weighted EPI Using an IDEAL Approach with Image Navigator"; Magentic Resonance in Medicine; vol. 73, pp. 964-972; Year: 2015.
Jo, Stephanie et al: "Musculoskeletal MRI Pulse Sequences: A Review for Residents and Fellows"; In: RadioGraphics; vol. 39, pp. 2038-2039; Year: 2019.

\* cited by examiner

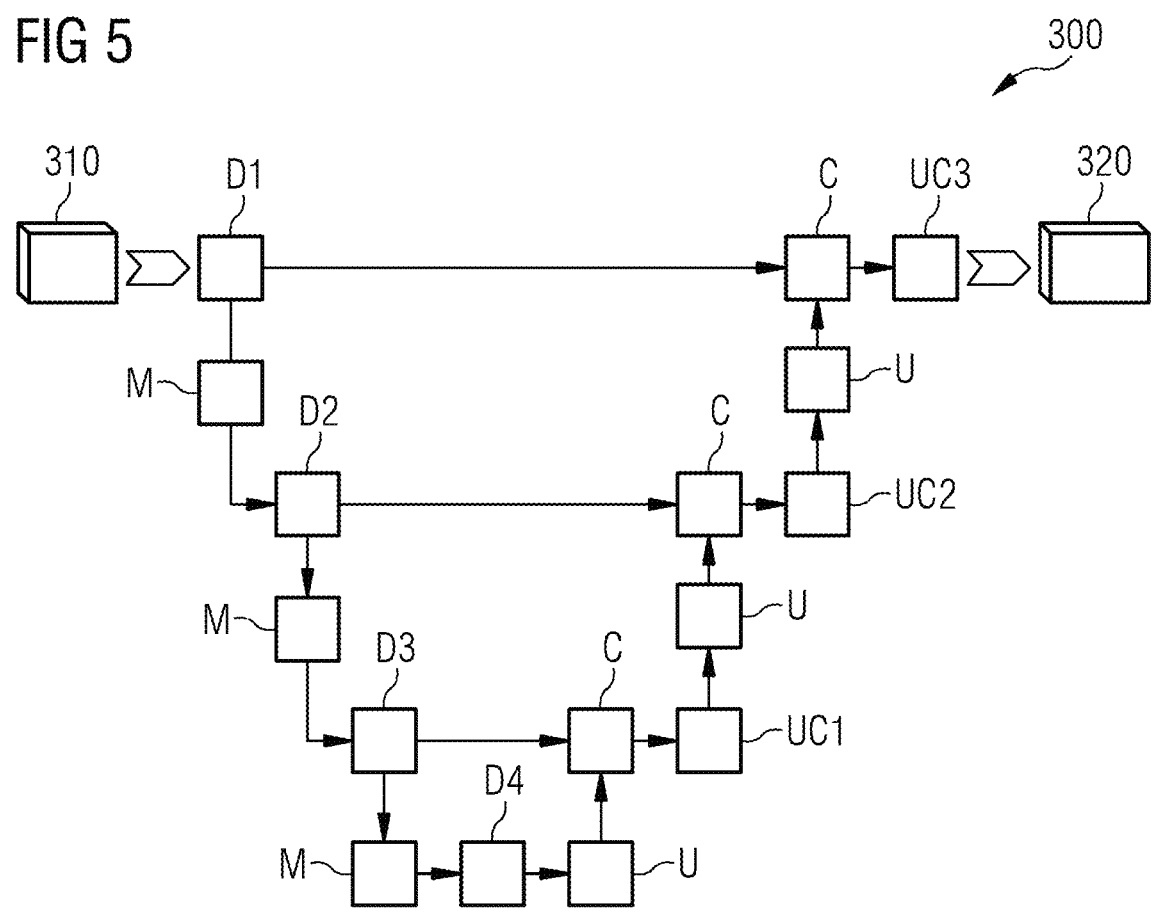

FAT SUPPRESSION USING NEURAL NETWORKS

CROSS REFERENCE TO RELATED APPLICATIONS

This patent application claims priority to German Patent Application No. 10 2021 208 406.0, filed Aug. 3, 2021, which is incorporated herein by reference in its entirety.

BACKGROUND

Field

The present disclosure relates to a method for determining a fat-reduced magnetic resonance (MR) image of an object under examination, to an apparatus for this purpose, and to a computer program and an electronically readable data storage medium.

Related Art

Insufficient fat-suppression often leads to artifacts in the MR images, in particular in the case of echoplanar imaging. Some artifacts are caused by the fat-signal component in the measured MR signal, which lies at a spectral offset of about −3.3 ppm with respect to the water peak, as is shown in FIG. 2. The water spectrum is shown here by 1, and is mainly responsible for the MR signals. Also shown is the fat signal 2 that is shifted with respect to the water peak by approximately 3.3 ppm. This additional fat signal can be suppressed in the MR imaging, for instance by spectral fat saturation methods such as, for example, those defined by CHESS or SPAIR. These methods are based on using an RF saturation pulse that is selected spectrally such that only the fat signal 2 is excited, with this saturation pulse being applied before the actual imaging, and the resultant magnetization then being dephased before the imaging. The frequency of the olefins 3 is very close to the water frequency, making spectral saturation impossible. Since the frequency of this fat component is almost identical to the frequency of water, this signal does not produce ghosting artifacts in echoplanar imaging, but this signal component of the olefins can cause an unwanted bright fat signal, in particular in echoplanar imaging.

A further option for fat saturation is to employ an inversion pulse, which is used as a 180° excitation pulse before the imaging. This pulse then excites both the fat and water constituents. Since the relaxation times of fat and water are different, however, an inversion time or wait time TI is employed, after which the actual, wanted signal is excited and the imaging is performed by signal detection. This wait time TI is selected such that the longitudinal magnetization of the fat components is 0 during the subsequent excitation. Consequently, only the water constituent is excited, and the fat does not contribute to the MR signal. By this method, it is possible to reduce the fat components of the olefins, but the method has the disadvantage of prolonging the imaging times as a result of the additional wait time TI, which equals about 200 ms. In addition, the signal-to-noise ratio is reduced, because not all the water signal can contribute to the MR signal as a result of the first inversion pulse.

BRIEF DESCRIPTION OF THE DRAWINGS/FIGURES

The accompanying drawings, which are incorporated herein and form a part of the specification, illustrate the embodiments of the present disclosure and, together with the description, further serve to explain the principles of the embodiments and to enable a person skilled in the pertinent art to make and use the embodiments.

FIG. 5 shows schematically a further use of the U-net architecture, in which the input and output images have different contrasts and resolutions, according to an exemplary embodiment of the present disclosure.

Figure 1:
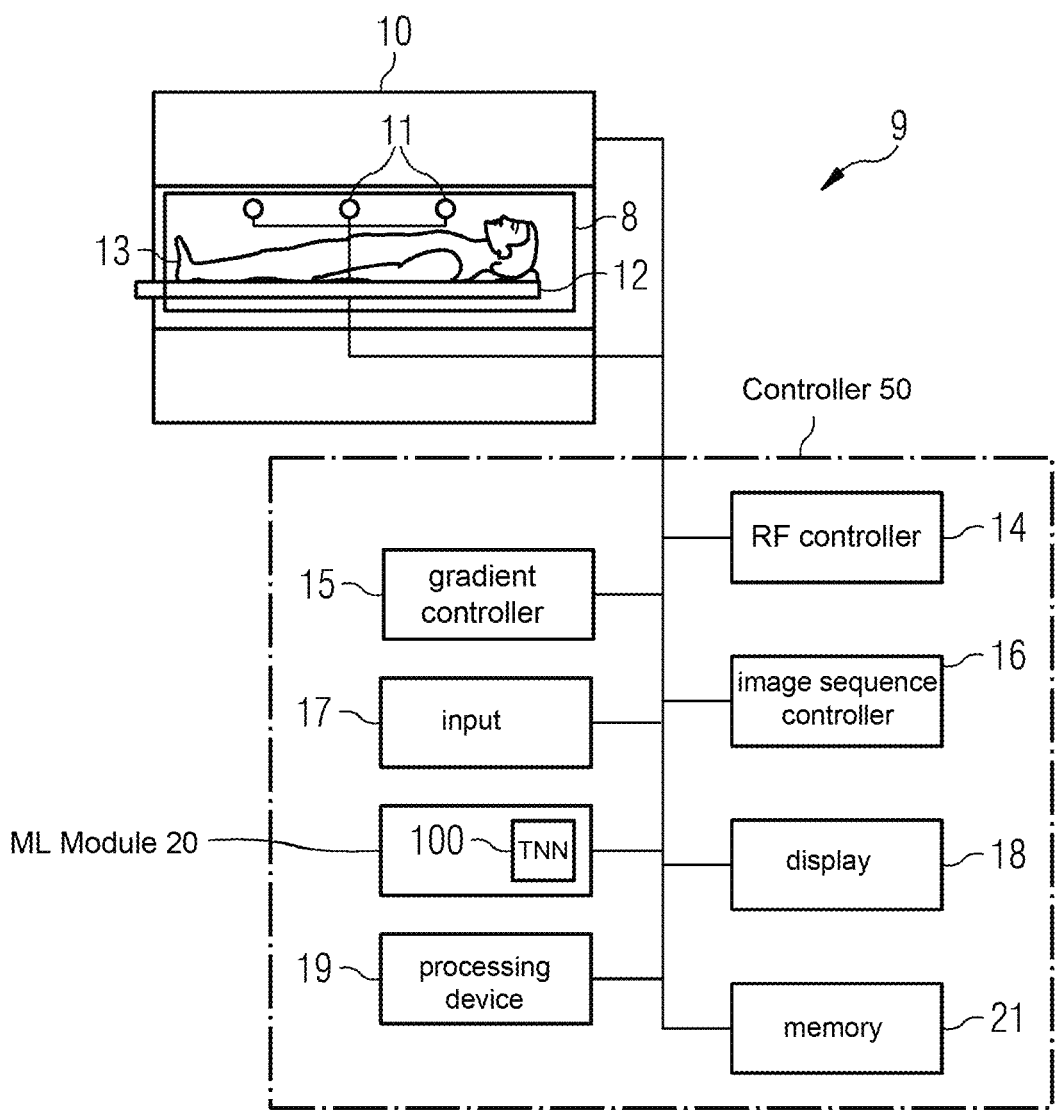
FIG. 1 shows an MR system according to an exemplary embodiment and which is configured to determine fat-reduced MR images.
Figure 2:
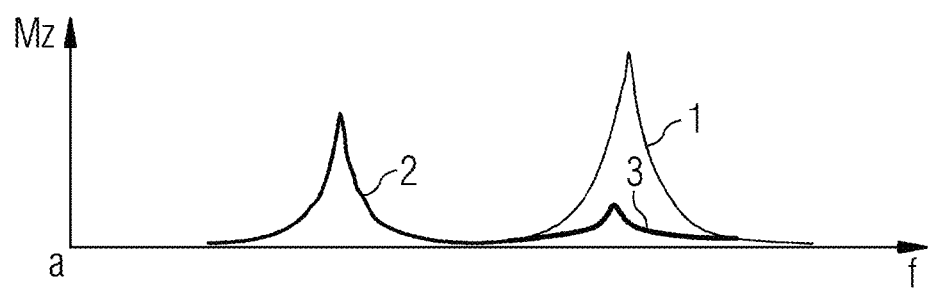
FIG. 2 shows schematically the spectrum of water and of the two fat constituents according to an exemplary embodiment of the present disclosure.

The exemplary embodiments of the present disclosure will be described with reference to the accompanying drawings. Elements, features and components that are identical, functionally identical and have the same effect are—insofar as is not stated otherwise—respectively provided with the same reference character.

DETAILED DESCRIPTION

In the following description, numerous specific details are set forth in order to provide a thorough understanding of the embodiments of the present disclosure. However, it will be apparent to those skilled in the art that the embodiments, including structures, systems, and methods, may be practiced without these specific details. The description and representation herein are the common means used by those experienced or skilled in the art to most effectively convey the substance of their work to others skilled in the art. In other instances, well-known methods, procedures, components, and circuitry have not been described in detail to avoid unnecessarily obscuring embodiments of the disclosure. The connections shown in the figures between functional units or other elements can also be implemented as indirect connections, wherein a connection can be wireless or wired. Functional units can be implemented as hardware, software or a combination of hardware and software.

An object of the present disclosure is to resolve the noted problems of the conventional techniques, and to produce fat-reduced MR images that have essentially no fat-signal components, yet without unnecessarily prolonging the acquisition time and also with the signal-to-noise ratio being not much lower compared with spectral fat saturation.

According to a first aspect of the disclosure, a method is provided for determining a fat-reduced MR image of a tissue under examination, which has, apart from other tissue types, two fat constituents of different resonance frequency. In a first step of the method, a first MR image is provided, which has, apart from the other tissue constituents, MR signals from essentially only one of the two fat constituents. In addition, the first MR image is applied to a trained artificial neural network, which has been trained by first MR training data as the input data, which data has, apart from the other tissue constituents, MR signals from essentially only the one of the two fat constituents, wherein second MR training data was used as the base knowledge in the training, which data has, apart from the other tissue constituents, essentially no MR signals from the two fat constituents. Furthermore, the MR output image from the trained neural network, to which the first MR image was applied, is determined, which MR output image is a fat-reduced image which has, apart from the other tissue constituents, essentially no MR signals from the two fat constituents.

The artificial neural network has now been trained such that the first MR training data as the input data still has the one fat constituent, whereas the base knowledge, i.e. the result data from the training, has, apart from the other tissue constituents, no MR signals from the two fat constituents. It is thereby possible to apply to the artificial neural network trained in this manner the first MR image, in which one of the two fat constituents is still contained in the signal, and the output image essentially no longer has any fat constituent components, because the neural network has been trained to recognize and to reduce a remaining fat constituent in the MR image.

In an exemplary embodiment, the first MR image and the first MR training data have been generated by an imaging sequence in which the one of the two fat constituents was suppressed by spectral fat saturation, while the other of the two fat constituents is still contained in the MR signal, which then forms the first MR image or the first MR training data respectively.

Furthermore, the second MR training data is generated by an imaging sequence in which a saturation inversion pulse suppresses the two fat constituents during the signal acquisition.

Since the time for producing the second MR training data is longer than the time for producing the first MR training data, and in particular for producing the first MR image, when using the trained neural network, the first MR image, which was generated using spectral fat saturation, can be used as the input data, and the artificial neural network generates an MR output image without the two fat constituents, similar to the image that was generated using the saturation inversion pulse, but without having to use this, thereby reducing the acquisition time overall.

The trained artificial neural network may be a convolutional U-shaped neural network, for instance a U-net, although other neural networks are also possible such as GAN networks (generative adversarial networks).

In an exemplary embodiment, the first MR image and the first and second MR training data are acquired by the echoplanar technique.

In addition, it is possible to determine or use a mask, which is used to select a subregion of the first MR image that contains image points having MR signals from the only one fat constituent, which mask is applied to the first MR image, and the subregion selected by the mask is applied instead of the entire first MR image to the trained artificial neural network. The mask restricts the image region in which, for example, can be expected the fat constituent that cannot be suppressed by spectral fat saturation. In the simplest case, the mask can be obtained by dividing the signal intensities, pixel by pixel, from one image acquired by spectral fat saturation and one image acquired by inversion saturation, and then partitioning into at least two image regions. The image regions are obtained from the pixel intensities of the division image. The partitioning can be performed, for instance, by simple thresholding, histogram analysis or a k-means clustering algorithm. Essentially, regions having a high value are assigned to the cluster in which the spectral fat saturation was not successful (fat is poorly saturated in the spectral image, strongly saturated in the inversion image); regions having a quotient that is lower relative thereto are assigned to the other cluster.

Furthermore, the first MR training data and the second MR training data can be acquired using different diffusion encodings.

It is possible here that the first MR image has a first diffusion encoding, with an additional second MR image being applied in addition to the first MR image to the artificial neural network. The additional second MR image can have the same slice position as the first MR image of an object under examination from which the MR images are acquired, and can have, apart from the other tissue constituents, essentially no MR signal from the two fat constituents. The MR output image can then have a diffusion encoding that differs from the first diffusion encoding. Likewise, the first MR image can have a first contrast and a first resolution, and an additional second MR image, which has a lower resolution than the first MR image and a second, different contrast, is applied in addition to the first MR image to the artificial neural network. The MR output image then has the first resolution and the second contrast.

Furthermore, the corresponding apparatus for determining the fat-reduced MR image is provided, which apparatus has the artificially trained neural network and is designed to work as explained above.

In addition, a computer program is provided, which has program means and can be loaded into a memory unit of a control apparatus in order to perform the steps of the above-described method when the program means are executed in the control apparatus.

An electronically readable data storage medium containing a computer program is likewise provided, which data storage medium is an electronic signal, optical signal, radio signal and/or a computer-readable storage device.

The features presented above and the features described below can be used not just in the corresponding explicitly presented combinations but also in other combinations unless explicitly stated otherwise.

An MR system 9, which can be used to generate a fat-reduced MR image, is explained with reference to FIG. 1. The MR system 9 has a magnet 10 for generating a polarization field B0, where a person under examination 13 arranged on a couch 12 is moved into the magnet 10 in order to acquire there spatially encoded magnetic resonance signals from the person under examination 13. The coils 11 used for the signal acquisition may be a body coil or local coils. In addition, a shim coil 8 is provided for correcting magnetic field inhomogeneities. By applying radiofrequency pulses and by switching magnetic field gradients, the magnetization produced by the polarization field B0 can be deflected out of the equilibrium position and spatially encoded, and the resultant magnetization is detected by the receive coils. The principles of how MR images can be produced by applying RF pulses and switching magnetic field gradients in various combinations and sequences are known to a person skilled in the art and are not explained further here.

The MR system also has a controller 50, which can be used to control the MR system 9. The controller 50 has an RF controller 14 for controlling and generating the RF pulses for deflecting the magnetization. A gradient controller 15 is provided for controlling and switching the necessary magnetic field gradients. An image sequence controller 16 controls the order of the magnetic field gradients, of the signal detection and of the RF pulses, where an operator can control the MR system via an input 17, and the generated MR images can be displayed on a display 18. A processing device 19 comprising at least one processor is provided for controlling the various units in the controller 50. In addition, a memory 21 is provided, in which can be stored, for example, program modules or programs, which can control the running of the MR system when they are executed by the processing device 19 or its processor. In addition, a module 20 is provided for machine learning, in which is stored a trained neural network 100. By means of the trained neural network 100, the module 20 is capable of generating from an input image containing a fat-signal component an output image having essentially no fat-signal components. In an exemplary embodiment, the controller 14 includes processing circuitry that is configured to perform one or more respective functions and/or operations of the controller 14. One or more components of the controller 14 may additionally, or alternatively, include processing circuitry that is configured to perform one or more respective functions and/or operations of the component(s).

A "machine learning" based approach is explained below, by which it is possible to remove unwanted fat constituents, for instance unwanted olefin fat signals, from the MR images, or reduce the component. To this end, the artificial neural network 40 is used in order to suppress the signal components from the olefins while retaining the wanted water signal.

A particular field of usage here is the use of echoplanar (EPI) images, because a single EPI slice can be acquired in seconds.

Figure 3:
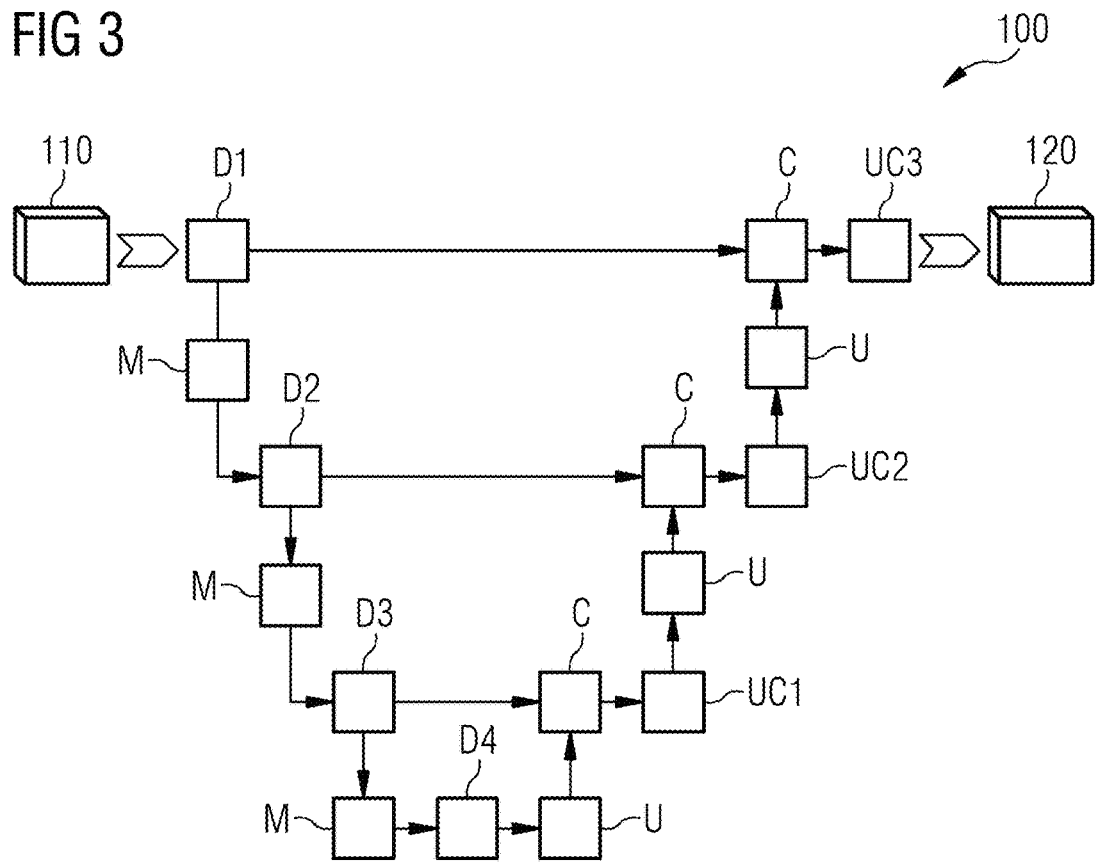
FIG. 3 shows schematically a U-net architecture of a trained neural network that can be employed to compute fat-reduced MR images according to an exemplary embodiment of the present disclosure.

FIG. 3 now shows a first usage case employing a trained neural network 100. This network 100 has been trained by first MR training data, for instance slices from a tissue under examination, where the one fat signal has been suppressed in the training data by spectral fat saturation, but the signal still contains the olefin signal components. The base knowledge for the training here consisted of MR images in which both fat constituents were suppressed, for instance using an inversion pulse, in which process the imaging takes place while the fat signals have no horizontal magnetization component. The training data can be obtained from EPI sequences having a plurality of slices, in which case the training data can be encoded for different diffusion encodings, i.e. different b-values, and different diffusion directions. For a good signal-to-noise ratio, the inversion pulse can be used to acquire the training data i.e. the base knowledge, repeatedly, and averaged training data can be used. With reference to FIG. 3, it is then possible to input into the trained artificial neural network a first MR image 110 or first MR images, where this may be an MR image in which only one of the two fat constituents is suppressed, for instance by spectral saturation. In this case, each MR image can represent the real channel and the imaginary channel, and therefore each of these channels is input separately. It is also possible, however, to perform the method on the magnitude images, in which case then only one image is used as the input image for the neural network 100, and not two as shown in FIG. 3. The U-shaped neural network is a "convolutional neural network" (CNN). In this U-shaped architecture, the first half of the network is used for feature extraction, and the ascending branch for increasing the resolution. As is known for such U-net architectures, the network 100 has different convolutions for reducing the resolutions, shown as D1 to D3 (down-convolution), between which is performed maximum extraction, represented by M in FIG. 3 (max pooling). In the ascending branch, U elements (up-sampling) and UC elements (up-convolution) are provided, and also concatenation steps represented by C. The first MR image 110, or the two channels of the first MR image, is now input into the trained neural network described above, where only one of the two fat constituents is suppressed in the MR image 110, namely the fat constituent at −3.3 ppm. The output image 120 is finally an MR image, or the two channels thereof, in which the two fat constituents, i.e. also the olefins, are suppressed, with the resolution equal to the resolution of the first MR image.

Figure 4:
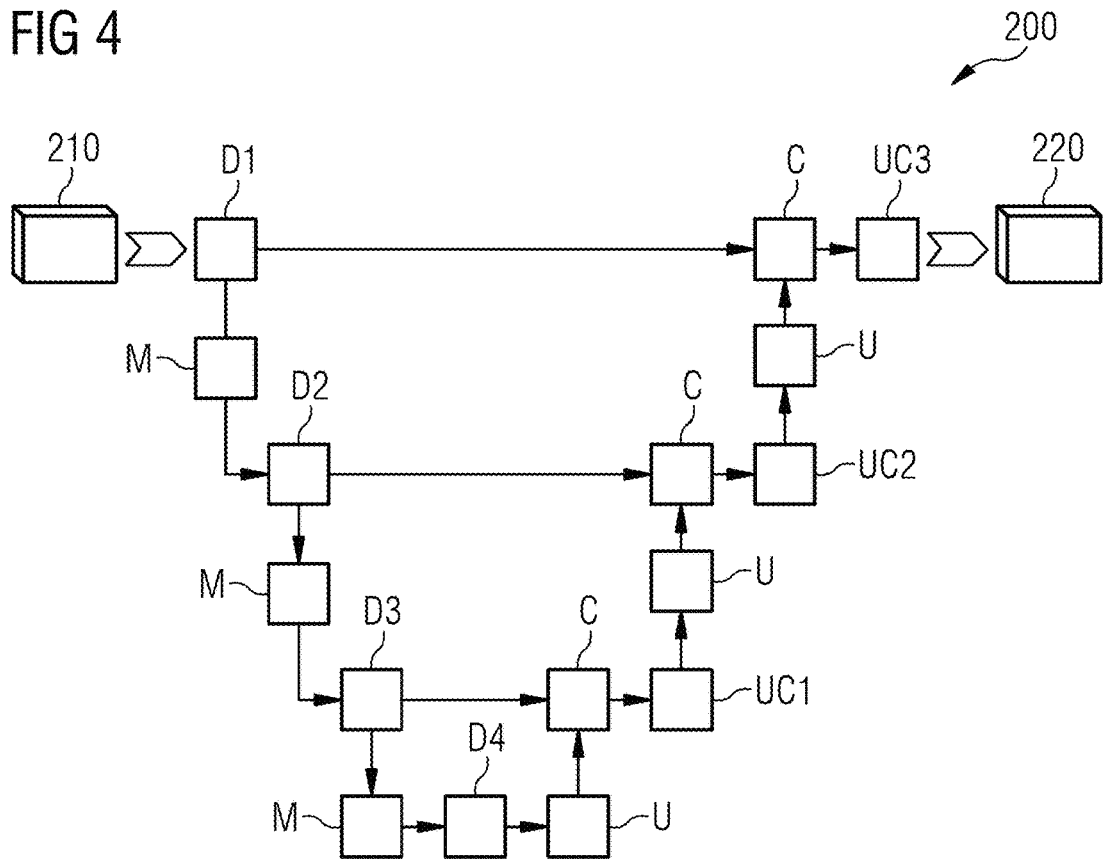
FIG. 4 shows a further use of the U-net of FIG. 3, in which additionally different diffusion weightings can be used, according to an exemplary embodiment of the present disclosure.

FIG. 4 now shows a further example of a trained neural network 200. In this embodiment, once again an input image in which only one fat constituent is suppressed is converted into an output image, which output image has a first diffusion encoding, i.e. a first arbitrary b-value. In addition, further additional input data, a second MR image without diffusion encoding, i.e. b=0, with saturation of the two fat constituents, for instance by an inversion pulse, is input, and also a third image without diffusion encoding, i.e. b=0, in which just the one fat constituent has been saturated by spectral fat saturation. Optionally, the mask for reducing the image region can be input as well. The output image is then once again an MR image having the first arbitrary b-value, the same diffusion encoding, in which image both fat constituents are again suppressed. The third image having b=0 is used to make the network more stable by means of patient-specific data (ground truth data). This embodiment has the advantage that more information about the object under examination is used as the input for the network, with the result that the output image 220 has fewer artifacts and the representation of the anatomy is improved. Since the MR signal acquisition with b=0 is present in every EPI diffusion measurement, the overall image acquisition time is prolonged only slightly in order to acquire the additional EPI volume using the inversion pulse. In this case, just as before, a plurality of acquisitions of the MR images, which have been prepared using the inversion pulse for fat saturation, can be averaged for the training phase to improve the signal-to-noise ratio in the training data.

In an exemplary embodiment, the network of FIG. 4 has been trained in a similar manner. If b0 means no diffusion encoding, bx an arbitrary diffusion encoding (b0, b50, b400, b1000), and fs means the spectral fat saturation, IR the saturation with inversion pulse, and final the improved objective, or output image, then b0_fs, b0_IR, bx_fs would be applied to the network of FIG. 4, where the output image is bx_final.

In the network of FIG. 3, the input image would then be b0_fs and the output image would be b0_final, or the input image would have any diffusion weighting bx_fs and the output image would then have the same diffusion weighting bx_final. As described above, B0_IR and bx_IR have a lower signal-to-noise ratio, and therefore it makes sense in the training not to make b0_final and bx_IR equal to b0_IR and bx_IR, but to a plurality of averages of b0_IR and bx_IR respectively.

Instead of the inversion pulse for producing the MR images that contain essentially neither of the two fat constituents, other fat saturation techniques that allow better fat saturation than the spectral saturation can be used; for instance various Dixon methods can be used.

A further exemplary method, which generalizes the elements described above, is described in connection with FIG. 5. In terms of design, the neural network 300 corresponds to the networks shown in FIGS. 3 and 4. The idea here is for the neural network to change input images 310 without fat saturation into images 320 with fat saturation, or in general to change images having a first contrast into images having a second contrast. It is possible to use as the input images 310, for example, a high-resolution first image having a first contrast, a lower-resolution image having the second contrast, and optionally a lower-resolution image having the first contrast. For example, an MR image of resolution 512×512 without fat saturation and acquired using a fast spin echo sequence can be used as an MR image 310, while using at the same time a lower-resolution image with fat saturation and a resolution of, for instance, 64×64. This lower-resolution image then has the second contrast, and the output image 320 then likewise has a resolution of 512×512 and a contrast equal to the contrast of the second, lower-resolution image.

In summary, the above method describes a possible way of improving further the fat saturation in MR images by using an appropriately trained neural network.

To enable those skilled in the art to better understand the solution of the present disclosure, the technical solution in the embodiments of the present disclosure is described clearly and completely below in conjunction with the drawings in the embodiments of the present disclosure. Obviously, the embodiments described are only some, not all, of the embodiments of the present disclosure. All other embodiments obtained by those skilled in the art on the basis of the embodiments in the present disclosure without any creative effort should fall within the scope of protection of the present disclosure.

It should be noted that the terms "first", "second", etc. in the description, claims and abovementioned drawings of the present disclosure are used to distinguish between similar objects, but not necessarily used to describe a specific order or sequence. It should be understood that data used in this way can be interchanged as appropriate so that the embodiments of the present disclosure described here can be implemented in an order other than those shown or described here. In addition, the terms "comprise" and "have" and any variants thereof are intended to cover non-exclusive inclusion. For example, a process, method, system, product or equipment comprising a series of steps or modules or units is not necessarily limited to those steps or modules or units which are clearly listed, but may comprise other steps or modules or units which are not clearly listed or are intrinsic to such processes, methods, products or equipment.

References in the specification to "one embodiment," "an embodiment," "an exemplary embodiment," etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described.

The exemplary embodiments described herein are provided for illustrative purposes, and are not limiting. Other exemplary embodiments are possible, and modifications may be made to the exemplary embodiments. Therefore, the specification is not meant to limit the disclosure. Rather, the scope of the disclosure is defined only in accordance with the following claims and their equivalents.

Embodiments may be implemented in hardware (e.g., circuits), firmware, software, or any combination thereof. Embodiments may also be implemented as instructions stored on a machine-readable medium, which may be read and executed by one or more processors. A machine-readable medium may include any mechanism for storing or transmitting information in a form readable by a machine (e.g., a computer). For example, a machine-readable medium may include read only memory (ROM); random access memory (RAM); magnetic disk storage media; optical storage media; flash memory devices; electrical, optical, acoustical or other forms of propagated signals (e.g., carrier waves, infrared signals, digital signals, etc.), and others. Further, firmware, software, routines, instructions may be described herein as performing certain actions. However, it should be appreciated that such descriptions are merely for convenience and that such actions in fact results from computing devices, processors, controllers, or other devices executing the firmware, software, routines, instructions, etc. Further, any of the implementation variations may be carried out by a general-purpose computer.

For the purposes of this discussion, the term "processing circuitry" shall be understood to be circuit(s) or processor(s), or a combination thereof. A circuit includes an analog circuit, a digital circuit, data processing circuit, other structural electronic hardware, or a combination thereof. A processor includes a microprocessor, a digital signal processor (DSP), central processor (CPU), application-specific instruction set processor (ASIP), graphics and/or image processor, multi-core processor, or other hardware processor. The processor may be "hard-coded" with instructions to perform corresponding function(s) according to aspects described herein. Alternatively, the processor may access an internal and/or external memory to retrieve instructions stored in the memory, which when executed by the processor, perform the corresponding function(s) associated with the processor, and/or one or more functions and/or operations related to the operation of a component having the processor included therein.

In one or more of the exemplary embodiments described herein, the memory is any well-known volatile and/or non-volatile memory, including, for example, read-only memory (ROM), random access memory (RAM), flash memory, a magnetic storage media, an optical disc, erasable programmable read only memory (EPROM), and programmable read only memory (PROM). The memory can be non-removable, removable, or a combination of both.

The invention claimed is:

1. A computer-implemented method, performed using one or more processors and a non-transitory computer-readable storage medium, for determining a fat-reduced magnetic resonance (MR) image of a tissue under examination that has, apart from other tissue constituents, two fat constituents of different resonance frequency, the method comprising:
providing a first MR image, which has, apart from the other tissue constituents, MR signals from only one of the two fat constituents;
applying the first MR image to a trained artificial neural network, which was trained by first MR training data as input data, the training data including, apart from the other tissue constituents, MR signals from only the one of the two fat constituents, and using second MR training data as a base knowledge, the second MR training data including, apart from the other tissue constituents, no MR signals from the two fat constituents; and
determining an MR output image from the trained artificial neural network, to which the first MR image was applied, as a fat-reduced MR image, wherein the fat-reduced MR image includes, apart from the other tissue constituents, no MR signals from the two fat constituents.

2. The method as claimed in claim 1, wherein the second MR training data has been generated by an imaging sequence in which a saturation inversion pulse suppresses the two fat constituents during signal acquisition.

3. The method as claimed in claim 1, wherein the first MR image and the first MR training data were generated by an imaging sequence in which the one of the two fat constituents was suppressed by spectral fat saturation, while another of the two fat constituents is still contained in the respective MR signals which were used to generate the first MR image and the first MR training data.

4. The method as claimed in claim 1, wherein the trained artificial neural network is a convolutional U-shaped neural network.

5. The method as claimed in claim 1, wherein the first MR image and the first and second MR training data were acquired by an echoplanar technique.

6. The method as claimed in claim 1, further comprising: determining a mask configured to select a subregion of the first MR image that contains image points having MR signals from only the one of the two fat constituents; and
applying the mask to the first MR image to select the subregion of the first MR image, wherein applying the first MR image to the trained artificial neural network comprises applying only the selected subregion selected by the mask to the trained artificial neural network.

7. The method as claimed in claim 1, wherein the first MR training data and the second MR training data have been acquired using different diffusion encodings.

8. The method as claimed in claim 7, wherein the first MR image has a first diffusion encoding, wherein the method further comprises applying a second MR image to the artificial neural network, the second MR image having a same slice position as the first MR image and having, apart from the other tissue constituents, no MR signals from the two fat constituents, wherein the second MR image includes a diffusion encoding that differs from the first diffusion encoding.

9. The method as claimed in claim 8, further comprising applying a third MR image to the artificial neural network, the third MR image having: the same slice position as the first MR image, apart from the other tissue constituents, only the one of the two fat constituents, and a diffusion encoding that differs from the first diffusion encoding.

10. The method as claimed in claim 1, wherein the first MR image comprises a first contrast and a first resolution, and wherein the method further comprises applying a second MR image to the artificial neural network, the second MR image having a low resolution compared with the first MR image and a second contrast that differs from the first contrast, wherein the MR output image includes the first resolution and the second contrast.

11. A computer program product embodied on the non-transitory computer-readable storage medium and which is directly loadable into a memory of a magnetic resonance device, when executed by the one or more processors of the magnetic resonance device, causes the magnetic resonance device to perform the method as claimed in claim 1.

12. A non-transitory computer-readable storage medium with an executable program stored thereon, that when executed, instructs a processor to perform:
providing a first MR image, which has, apart from the other tissue constituents, MR signals from only one of the two fat constituents;
applying the first MR image to a trained artificial neural network, which was trained by first MR training data as input data, the training data including, apart from the other tissue constituents, MR signals from only the one of the two fat constituents, and using second MR training data as a base knowledge, the second MR training data including, apart from the other tissue constituents, no MR signals from the two fat constituents; and
determining an MR output image from the trained artificial neural network, to which the first MR image was applied, as a fat-reduced MR image, wherein the fat-reduced MR image includes, apart from the other tissue constituents, no MR signals from the two fat constituents.

13. An apparatus for determining a fat-reduced magnetic resonance (MR) image of a tissue under examination that has, apart from other tissue constituents, two fat constituents of different resonance frequency, the apparatus comprising:
an artificial trained neural network; and
a processing device configured to:
provide a first MR image including, apart from the other tissue constituents, MR signals from only one of the two fat constituents;
apply the first MR image to the trained artificial neural network, wherein the artificial trained neural network has been trained by first MR training data as input data, the first MR training data including, apart from the other tissue constituents, MR signals from only the one of the two fat constituents, and using second MR training data as a base knowledge, the second MR training data including, apart from the other tissue constituents, no MR signals from the two fat constituents; and
determine an MR output image, from the trained artificial neural network to which the first MR image was applied, as a fat-reduced MR image that includes, apart from the other tissue constituents, no MR signals from the two fat constituents.

14. The apparatus as claimed in claim 13, wherein the second MR training data has been generated by an imaging sequence in which a saturation inversion pulse suppresses the two fat constituents during signal acquisition.

15. The apparatus as claimed in claim 13, wherein the first MR image and the first MR training data were generated by an imaging sequence in which the one of the two fat constituents was suppressed by spectral fat saturation, while the other of the two fat constituents is still contained in the respective MR signals which were used to generate the first MR image and the first MR training data.

16. The apparatus as claimed in claim 13, wherein the trained artificial neural network is a convolutional U-shaped neural network.

17. The apparatus as claimed in claim 13, wherein the first MR image and the first and second MR training data were acquired by the echoplanar technique.

18. The apparatus as claimed in claim 13, wherein the processing device is further configured to:
determine a mask configured to select a subregion of the first MR image that contains image points having MR signals from only the one of the two fat constituents; and
apply the mask to the first MR image to select the subregion of the first MR image, wherein applying the first MR image to the trained artificial neural network comprises applying only the selected subregion selected by the mask to the trained artificial neural network.

19. The apparatus as claimed in claim 13, wherein the first MR training data and the second MR training data have been acquired using different diffusion encodings.

20. The apparatus as claimed in claim 19, wherein:
the first MR image has a first diffusion encoding; and
the processing device is configured to:
apply a second MR image to the artificial neural network, the second MR image having a same slice position as the first MR image and having, apart from the other tissue constituents, no MR signals from the two fat constituents, the second MR image including a diffusion encoding that differs from the first diffusion encoding; and
apply a third MR image to the artificial neural network, the third MR image having: the same slice position as the first MR image, apart from the other tissue constituents, only the one of the two fat constituents, and a diffusion encoding that differs from the first diffusion encoding.

* * * * *